United States Patent [19]

Weinrib

[11] Patent Number: 4,793,349
[45] Date of Patent: Dec. 27, 1988

[54] NEEDLE HOLDER FOR SURGERY

[76] Inventor: Harry P. Weinrib, 2644 W. Estes Ave., Chicago, Ill. 60645

[21] Appl. No.: 839,643

[22] Filed: Mar. 13, 1986

Related U.S. Application Data

[63] Continuation-in-part of Ser. No. 648,583, Sep. 10, 1984, abandoned.

[51] Int. Cl.⁴ .................. A61B 17/06; A61B 17/28
[52] U.S. Cl. .................................. 128/340; 128/321
[58] Field of Search .................. D28/55; D24/23, 26, D24/27; 128/340, 336, 337, 321, 334 R, 354, 346, 354

[56] References Cited

U.S. PATENT DOCUMENTS

| | | | |
|---|---|---|---|
| D. 233,864 | 12/1974 | McClure | D28/5 |
| D. 263,502 | 3/1982 | Tartaglia | 128/340 |
| D. 268,207 | 3/1983 | Tartaglia | 128/340 |
| 695,292 | 3/1902 | Ermold | 128/340 |
| 705,742 | 7/1902 | Dunham | 128/340 |
| 791,322 | 5/1905 | Clayton | 128/340 |
| 809,244 | 1/1906 | Blomquist | 294/99.2 |
| 1,386,436 | 8/1921 | Smith | 128/354 |
| 1,537,793 | 5/1925 | Bates | 128/354 |
| 1,610,925 | 12/1926 | Bryan | 128/354 |
| 1,704,992 | 3/1929 | St. Elmo Sanders | 128/340 |
| 2,376,448 | 5/1945 | Neugass | 128/354 |
| 2,397,823 | 4/1946 | Walter | 128/321 |
| 2,860,537 | 11/1958 | Ferguson | 81/43 |
| 2,998,649 | 9/1961 | Miller et al. | 30/131 |
| 3,120,847 | 2/1964 | Caveness | 128/340 |
| 3,140,715 | 7/1964 | Whitton, Jr. et al. | 128/321 |
| 3,349,772 | 10/1967 | Rygg | 128/340 |
| 3,367,336 | 2/1968 | Eizenberg | 128/321 |
| 3,398,746 | 8/1968 | Abramson | 128/340 |
| 3,653,389 | 4/1972 | Shannon | 128/354 |
| 3,677,112 | 7/1972 | Keniston | 81/43 |
| 3,906,957 | 9/1975 | Weston | 128/354 |
| 3,916,909 | 11/1975 | Kletschka et al. | 128/354 |
| 3,921,640 | 11/1975 | Freeborn | 128/321 |
| 3,972,333 | 8/1976 | Leveen | 128/318 |
| 3,977,410 | 8/1976 | Huston et al. | 128/354 |
| 4,044,771 | 8/1977 | Wannag | 128/354 |
| 4,212,305 | 7/1980 | LaLay | 128/354 |
| 4,385,628 | 5/1983 | Straith | 128/321 |
| 4,446,866 | 5/1984 | Davison | 128/340 |
| 4,452,106 | 6/1984 | Tartaglia | 81/43 |
| 4,461,297 | 7/1984 | Sutter | 128/334 |
| 4,506,669 | 3/1985 | Blake, III | 128/334 |
| 4,660,287 | 4/1987 | Decker | 30/339 |

FOREIGN PATENT DOCUMENTS

| | | | |
|---|---|---|---|
| 3023671 | 1/1982 | Fed. Rep. of Germany . | |
| 2491325 | 4/1982 | France . | |
| 1009441 | 4/1983 | U.S.S.R. | 128/321 |
| 20631140 | 6/1981 | United Kingdom . | |

Primary Examiner—Richard C. Pinkham
Assistant Examiner—Gary Jackson
Attorney, Agent, or Firm—Fitch, Even, Tabin & Flannery

[57] ABSTRACT

A hand held surgical needle holder for turning and gripping microsurgical needles. The needle holder is of the tweezer type with two spaced tongs having a cylindrical central portion. Pointed tips on the prongs are brought toward each other by pressure to grip the needle. One of the tips is hooked and extends beyond the end of the other tip member. The needle is held between the hooked surfaces as the cylindrical central portion is rotated to spin the needle in an arc.

9 Claims, 2 Drawing Sheets

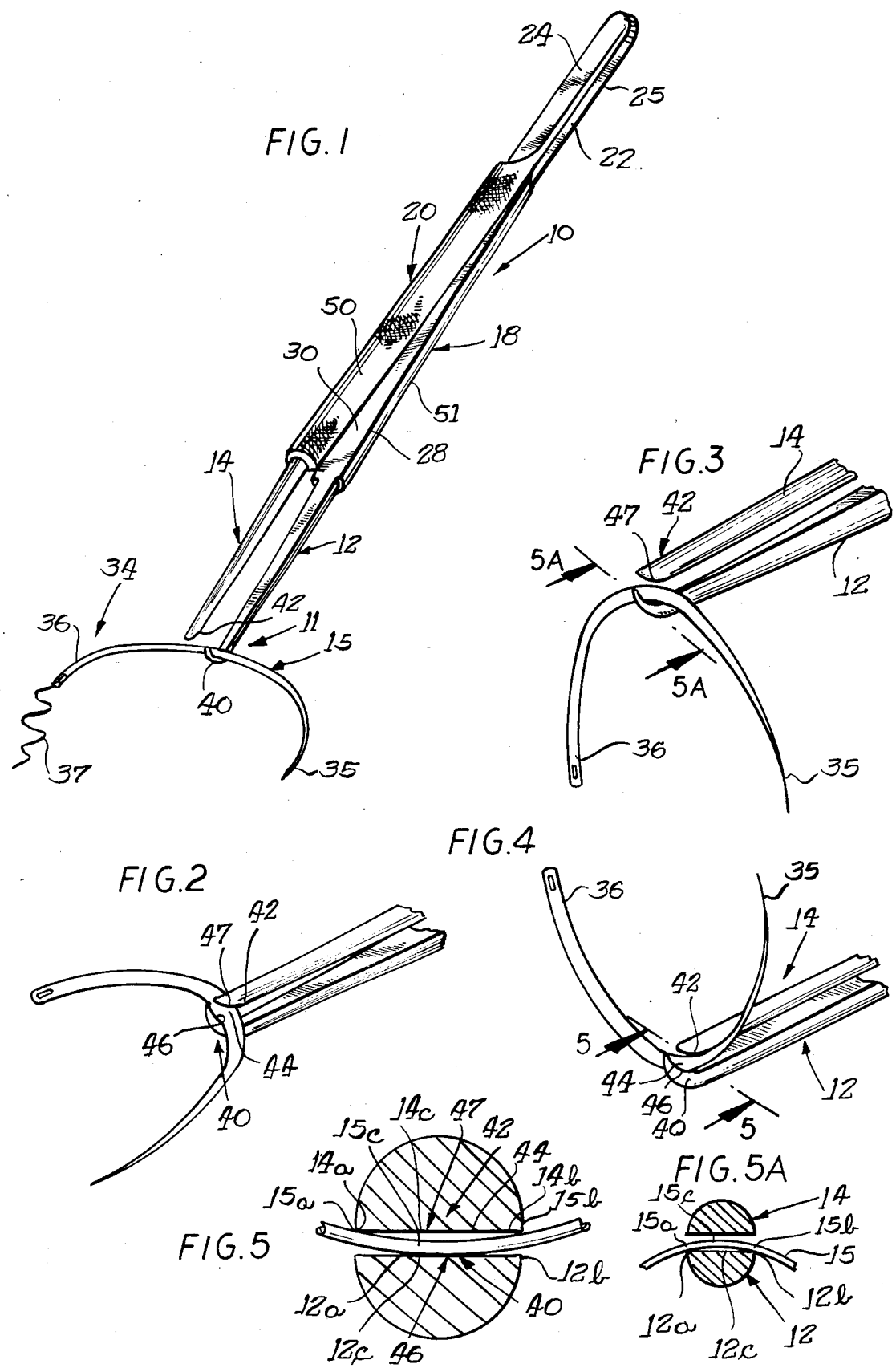

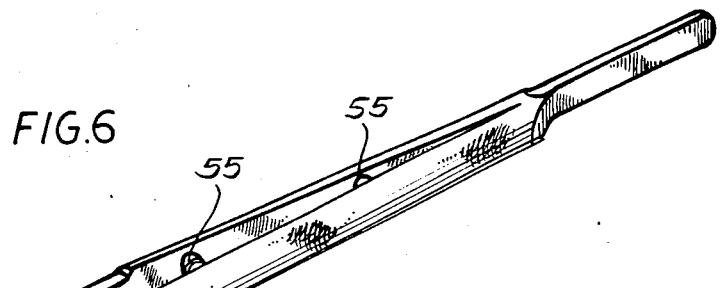
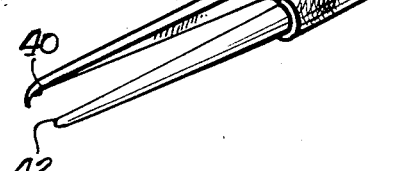
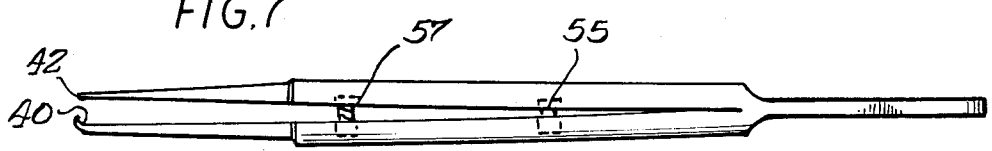
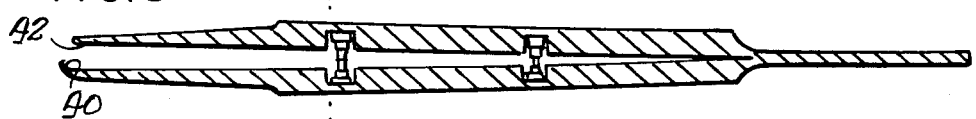
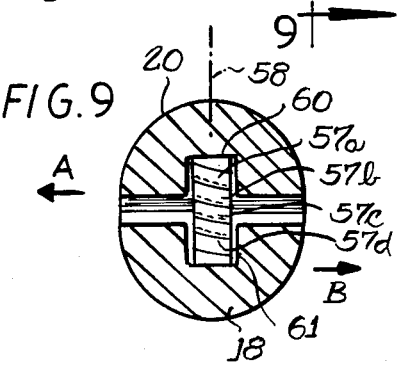
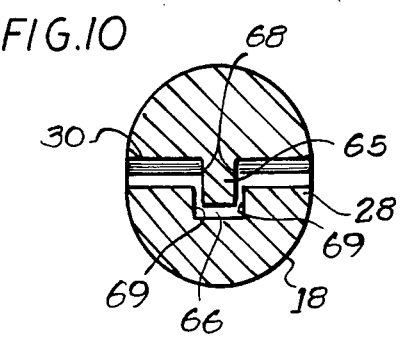
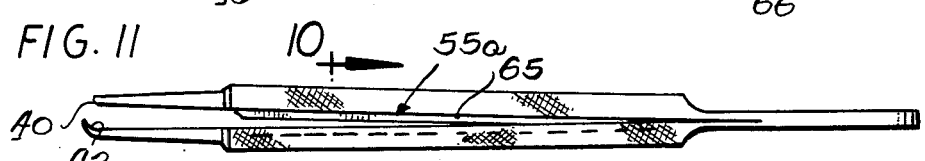
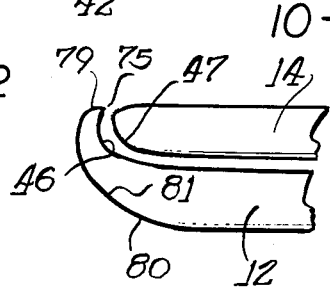
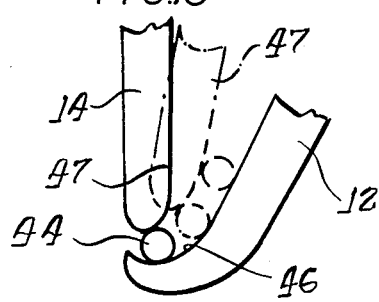

4,793,349

NEEDLE HOLDER FOR SURGERY

BACKGROUND OF THE INVENTION

This application is a continuation-in-part application of pending application Ser. No. 648,583 filed Sept. 10, 1984 now abandoned entitled "Needle Holder For Surgery".

FIELD OF INVENTION

This invention relates to a needle holder used in microsurgery and, more particularly, to a needle microinstrument or holder which can be used with a rotational technique and which orients the needle into proper position during pickup of a miniscule needle used in microsurgery.

DESCRIPTION OF THE PRIOR ART

The prior art needle holders used in microsurgery today are of two types. The first of which is a generally scissor-like instrument which has a pair of pivoted levers joined at a common pivot and handle at one end and a pair of jaws which are opened and closed by moving the handle at the other end. The other type of needle holder used in microsurgery is of the tweezer or forceps type in which the two spaced tongs are pivoted at one end and are brought together at the other end by finger pressure to grip the needle. Examples of these two types of microsurgery needle holders are shown in a microsurgery catalogue published by Accurate Surgical and Scientific Publishing Corporations, at 300 Shames Drive, Westbury, N.Y. 11590, at pp. 10–11, copyrighted Fall of 1982. Scissor action needle holders can not be used with a rotational microsurgical technique for which the microinstrument of the present invention is particularly suited by way of its construction. More specifically, the needle holder of the present invention is particularly useful with a rotational technique of a microsurgeon who rests a portion of his hand on a working surface in a position of stability to suppress tremors of the hand while imparting a spinning or pencil rolling type of movement to the microinstrument to swing the needle through an arcuate path to penetrate tissue.

In this rotational technique, the needle holder is positioned between the thumb and the middle finger and the thumb holds the needle on the middle finger and imparts a spindle-like rotation to the microinstrument about the longitudinal axis thereof providing a motion that is smooth and precise, even as seen under high magnification. The rotational technique allows the curved microsurgical needle to be spun through its natural arc of rotation thereby minimizing tissue damage as the needle enters the vessel wall and curves therethrough in an arc and exits perpendicularly to a vessel wall. This minimizes trauma to delicate layers of the vessel wall.

The microsurgical needles are often picked up while viewed under 20 to 25 magnification of a microscope. To the human eye, without magnification, the needles are as fine as a baby's eyelash having a diameter of about 70 microns, i.e., 0.070 millimeter. The thread connected to one end of the needle is finer than human hair and is gossamer fine. If the microsurgical needle is grasped and is bent by the needle holder, then it is no longer useful. In other instances, the needle holders allow the needle to pop out of the holder, particularly when used by less inexperienced microsurgeons; and it is most difficult to locate a microsurgical needle once it has popped out of the needle holder. After a successful gripping of the curved microsurgical needle with the conventional needle holders in the dominant hand of the microsurgeon, it is then necessary to take a second hold with the non-dominant hand and grip the needle tip and rotate the needle tip through a 90° arc and then release the tip and re-grip the needle tip and turn it an additional arc so that the needle is properly oriented with the point up and ready for the rotational and spinning movement.

It will be understood that the microsurgeon often works for many hours and does numerous stitches so that the manipulations of the microsurgical needles through one or two separate arcuate turns is time-consuming and as well physically taxing. Any slowdown of the surgery adversely affects the patient and his recovery. The tips of the forceps-like needle holders are very fine and may be as sharp as pinpoints. Microsurgery must be learned, and the ordinary surgeon using macroinstruments and macro hand and arm movements without magnification can not do microsurgery without substantial instruction and practice. Also, the instruments used for macrosurgery are inapplicable to the problems solved by the present invention. Macroinstruments are not used with such movements, such that, for example, a one-inch of the instrument may take it out of the field of view as does a microsurgical needle viewed under the microscope.

It is easy for these fine thin pointed tips of the microinstrument to move out of proper planar alignment, i.e., to twist relative to one another between the opened position and the fully closed, tightly gripping position, with the result that the needle is not properly gripped and locked in position as is desired. That is, it is most desirable that the gripping jaws be held in alignment at all times between their fully opened and fully closed positions so that they do not move or twist relative to one another causing a loss of a wrench-like gripping action on the needle which is to be spun with the rotational technique.

SUMMARY

This invention relates to microinstrument or needle holder which is used to grasp and lift curved microsurgical needles and then rotate the needles through an arc to a predetermined position with the pointed end of the needle pointing upwardly whereupon the whole instrument can be spun with the rotational technique for suturing blood vessels, nerves, arteries and other tissue, while being viewed under a high-powered microscope. Numerous sutures are done and the elimination of the usual operation to grip the needle tip with a second instrument held in a non-dominant hand and to turn it through one or more successive turns to bring the point upwardly is of great advantage in reducing the time involved in the surgery and in the fatigue of the microsurgeon.

Additionally, the microsurgical needle holder of this invention is particularly suited for the rotational technique used in microsurgery because it has a tubular or pencil-like body which allows it to be gripped between the thumb and the middle finger and to be spun about its longitudinal axis in the nature of a pencil-rolling motion between the thumb and the middle finger. The microsurgical needle holder of the present invention has one jaw with a hook formed thereon for hooking under and lifting a curved needle from a supporting surface. The hook allows the needle to be lifted from the support and allows the needle to rotate down and a curved surface on the other jaw cooperates with the curved surface on the end of the hooked end of the needle holder to automatically rotate the needle through a 180° arc merely by closing the jaws with the curved surfaces causing the portion of the needle therebetween to roll 180° whereupon the needle is firmly clamped therebetween.

In the preferred needle holder, the very fine tips which are, for example, 0.001 or 0.002 inch in width, are held aligned throughout the full extent of their opening and closing movements to prevent their twisting relative to one another as could bend the needle or as could cause a needle to pop out by an alignment means. Thus, there is a continually guiding of the tips for co-planar movement throughout the operating stroke of the jaws between their fully opened and fully closed positions. The preferred alignment means comprises a convolute spring which also provides a spring force to urge the jaws or tongs to their open position.

BRIEF DESCRIPTION OF THE DRAWINGS

FIG. 1 is a perspective view of a needle holder constructed in accordance with the preferred embodiment of the invention and embodying the novel features of the invention.

FIG. 2 is a view of the needle holder lifting a needle from a supporting surface.

FIG. 3 illustrates the curved needle having been lifted from the supporting surface with the needle having swung its ends downwardly.

FIG. 4 illustrates the needle having been rotated through 180° from the FIG. 3 position.

FIG. 5 is an enlarged cross-sectional view taken substantially along the line 5—5 of FIG. 4.

FIG. 5A is an enlarged cross-sectional view taken substantially along the line 5A—5A of FIG. 3.

FIG. 6 is a perspective view illustrating convoluted spring serving to align the tips of the needle holder.

FIG. 7 is a side elevational view of the needle holder of FIG. 6.

FIG. 8 is a longitudinal cross-sectional view of the needle holder and convolute springs.

FIG. 9 is an enlarged, transverse cross-sectional view taken along the line 9—9 of FIG. 8.

FIG. 10 is an enlarged cross-sectional view taken along the line 10 of FIG. 11.

FIG. 11 illustrates another embodiment of the invention in which the alignment means comprises an elongated key and receiving slot for the key.

FIG. 12 is a view of how to manufacture the tips of the needle holder.

FIG. 13 is a diagramatic illustration showing the needle rolling along the curved surface of the holder.

DESCRIPTION OF THE PREFERRED EMBODIMENT

Referring now to the drawings for purposes of illustration, there is illustrated a surgical needle holder or microinstrument 10 having a gripping end 11 including first and second tips or ends 12 and 14 which are movable between the open position shown in FIG. 1 and the closed position shown in FIG. 4 to grip a microsurgical needle 15 for use in microsurgery. The microsurgical needle holder includes a first section or half 18 and a second substantially identical half 20 with the halves being biased apart to the open position and being joined at a rearward end portion 22 of the microinstrument. For instance, the end 22 may be formed by the two halves being flattened at 24 and welded together along a seam line 25, the halves 18 and 20 are thus hinged together at the rearward flat portion 22 with the halves biased to the open position shown in FIG. 1. As the surgeon compresses the halves toward each other he brings the facing longitudinal, inner flat surfaces 28 and 30 toward one another which also brings the tips 12 and 14 into the grasping position shown in FIGS. 3-5.

The microsurgical needle 15, which is to be lifted from a supporting surface such as a horizontal planar surface 34 (in FIG. 1) is generally disposed in a horizontal position with its point 35 resting on the horizontal surface 34 and with its thread end 36 also resting on the flat horizontal surface. The microsurgical needles are much smaller than depicted in FIGS. 1-5A, and they have been enlarged only for purposes of illustration; and, as viewed in these FIGURES, the needles 15 have been magnified 20 or 25 times to appear as they would be under a microscope. In point of fact, the needles are as fine as a baby's eyelash, having a diameter of about only 70 microns, and a fine nylon thread 37 attached to the thread end 36 is finer than a human hair and is gossamer fine. It will be appreciated that such a fine microsurgical needle can be bent if it is roughly handled and that once bent, it can no longer be used. The needles are difficult to grip by those who are not highly trained in microsurgery; and when a surgeon makes numerous stitches in a microsurgical operation, it is to be understood that an occasional needle may pop out of the grasp of the instrument and be lost with the instrmments heretofore used.

Typically, the microsurgeon with a prior art needle holder grasps the needle with his dominant hand, and with a forceps in his non-dominant hand, he then grasps the needle end 35 with the forceps and rotates the needle point 35 pp into the operative position shown in FIG. 4 in which the point 35 of the needle is pointed upward with the thread bearing end 37 being likewise pointed upward. In this position, the needle point 35 is ready to be rotated through a piece of tissue, such as a human vessel for anastomizing blood vessels together. Manifestly, the particular end uses of the microsurgical instrument can vary considerably. Because the microsurgery may take hours to perform and may involve numerous stitches, it is important that the instrument be designed to facilitate the work of the surgeon and to reduce his fatigue from use of the instrument.

In accordance with the present invention a microsurgical needle 15 may be easily lifted from the supporting surface 34 and rotated automatically through the positions shown in FIGS. 2, 3 to the operative position shown in FIG. 4 in which the point 35 is uppermost without the use of a second forceps and without manipulation of the tip by the second instrument, as above-described. More specifically, in accordance with the present invention, the microsurgical instrument is provided with the hooked end 40 on the tip 12 which is used to hook under the needle and allows the needle to be lifted from the horizontal surface 34 with the needle then automatically winging by gravity downwardly to a position in which the point 35 and the thread end 37 are pointing downwardly as shown in FIG. 3. In this position, the upper tip 14 is still spaced from the lower tip 12 as showing FIG. 5A and by the simple action of depressing the upper half 20, a needle rotating end 42 on the tip 14 engages a central rotating section 44 of the needle and rotates the needle through 180° between the hanging position of FIGS. 3 and 5A to the operative position of FIG. 4. This rotation is achieved in the present invention by having a first curved surface 46 on the hooked end 40 and having a curved surface 47 on the needle rolling end 42, such that when the curved surface 47 engages the top surface of the central section 44 of the needle, and rolls it along the curved surface 46 a turning torque is imparted to the needle to spin the needle through an arc whereupon the needle will be clamped between the curved surfaces 46 and 47, as shown in FIG. 4. The preferred surfaces 46 and 47 which do the rotating are curved in the fore and aft direction but when viewed in a transverse direction, as shown in FIGS. 5 and 5A, have a generally straight line transverse surfaces 46 and 47 engagement with the needle. The surfaces 46 and 47 have preferably flat straight line profiles when viewed in the transverse direction as shown in FIGS. 5 and 5A. Initially, as best seen in FIG. 5A, the needle when it is lifted by the lower tip 12 rests with points 15a and 15b of the needle engaging outer edges 12a and 12b of the tip with the curved central portion 15c of the needle spaced from the central portion 12c of the tip. When the upper tip is brought into engagement with the top surface of the needle's curved central portion 15c the upper tip rotates the needle about the points 12a and 12b with the curved portion 15c moving downwardly and inwardly between the closing jaws of tips 14 and 12 until the curved needle portion 15c is brought into engagement with lower central portion 12c of the lower tip 12. At the completion of the rotation, the needle portions 15a and 15b are engaging the edges 14a and 14b of the upper tip 14 and are holding the central portion 15c of the needle flat against the central portion 12c of the lower tip. The central portion 14c of the upper tip will now be spaced from the central portion 15c of the needle. Thus, the needle will be clamped at three places 15a, 15c and 15b by the respective three pressure points of edge 14a of the upper tip 14, central portion 12c of the lower tip 12, and edge 14b of the upper tip. The exact clamping surface engagement may be greater than depicted depending upon the curvature of the needle and the sizes of the tips but these above-described points are the surfaces having the greatest pressure contact to do the clamping.

The tips are sharp and as pointed as needles, and the movements thereof are only about 8 mm. between opening and closing. The needles are so fine that if drawn to scale they would appear only as a fine small line adjacent the tip hook 40 and rolling surface 46. Movement of the tip as much as one-inch moves the needle out of the microscopic field at which it is being viewed.

The usual microsurgical needles range from about 50$\mu$ to 200 $\mu$mm. in diameter with 0.70 mm. being a common size. To cause a rolling action of the microsurgical needle along the curved surface of the hooked end 40 and to obtain a good tight grip on the needle after locking the preferred range of the radius for the curved surface for the hooked end is 1 to 3 mm. and the preferred range for the radius of the needle rolling surface 46 for the tip 14 is between about 1 mm and 3 mm. The tips of the needle holder appear as needle sharp points to the naked eye and they usually are only in the range of 500$\mu$ to 2 mm. in diameter. Because the pointed tips are so fine and sharp, the deflection laterally, i.e., a twisting movement of only a few millimeters causes problems in properly gripping the needle. Since the tips are often five or six inches from the tip ends, the tips have a long unsupported length that can lead to such deflections particularly when the surgeon is twisting the needle holder.

Also in accordance with the present invention, the preferred shape for the microinstrument is that of substantially cylindrical or tubular member when the halves 18 and 20 are brought together, so that the instrument may be rotated about its longitudinal axis. More specifically, the tubular central section of the instrument is laid along the middle finger of a hand resting on a surface to suppress tremors, and the thumb is rotated along the tubular surface to impart a spindle-like rotation to the instrument along its longitudinal axis on the middle finger thereby turning the needle through a natural arc of rotation to move the needle point 35 into and through tissue such as a wall. The illustrated instrument may be formed as a one-piece metal cylinder with a conical end which is then severed longitudinally to provide the two equal halves 18 and 20 to provide the facing flat surfaces 28 and 30 leaving outer rounded semi hemispheric walls 50 and 51 on the halves, as best seen in FIG. 1 and leaving the semi-conical tips 12 and 14. These semi-hemispherically wall surfaces are preferably knurled to facilitate the grip of the instrument by the surgeon.

Preferably, as shown in FIGS. 6-9, the microinstrument includes an alignment mean 55 which serves to assure that the hooked end 42 and the needle rolling end 42 stay in the same plane of closing movement and do not twist or move laterally relative to one another as indicated by the diagrammatic arrows A and B shown in FIG. 9. The preferred alignment means is disposed within the cylindrical confines of the rotatable tool and preferably acts for the entire movement of the instrument between its open and closed positions. By way of example, the tips may open to about 8 millimeters between them with halves 18 and 20 being disposed at an angle of 20°. The illustrated and preferred alignment means 55 comprises at least one convolute spring 57 which is seen in FIG. 9 comprises a plurality of wound spring coils 57a, 57b, 57c and 57d wound helically one within the other and each coil having a sliding movement with adjacent coils relative as the spring is expanded and collapsed about a central axis 58 through the coils. The coils freely slide against each other and when one tip 12 or 14 tries to move laterally as shown by the directional arrows A and B in FIG. 9 the sides of coils abut and stop this lateral shifting of the tips relative to each other and to the coils. The coil springs also provide a spring or biasing force to base the device to its open position.

The upper coil 57a is seated in a circular recess or bore 60 (FIG. 9) formed in the upper half 20 of the instrument and the lower coil 57d is seated in a lower cylindrical recess 61 in the lower half 18 of the instrument. Because the coils are nested one within the other, they will not allow the halves to move laterally as shown by the directional arrows A and B shown in FIG. 9 as would cause misalignment of the very fine tips 12 and 14. Herein, the respective convolute springs are separated into two functions with the spring 55 adjacent the closed end doing the guiding at the wider apart spacing of the tips and the spring 55 adjacent the tips guiding the tips through their last three millimeters of movement. The preferred spring force from the convolute springs is small, e.g. only 0.2 lbs. of opening force.

As an alternative embodiment to the convoluted springs 57 shown in FIGS. 6-9, another alignment means 55a may be used and this includes an elongated rectangular key 65 for fitting into a complementary shaped slot 66 in the lower half 18 of the instrument. The key 65 and slot 66 run the substantially full length along the flat inner surfaces 28 and 30 of the cylindrical halves 18 and 20 so that a portion of the key 65 always is positioned for sliding engagement with the vertical side walls 69 on the keyway slot 66 as shown in FIG. 10. There is a substantial advantage in always maintaining the alignment by either the alignment devices 55 and 55a as contrasted to the prior art separable pins and holes wherein only during the final closing movement will the pin engage walls of the hole to try to center during the final gripping action. Because the points 12 and 14 are so sharp on the ends of the microsurgical instrument, e.g. about 0.70 mm., the precision of the planar closing movement is needed more than with the macrosurgical tools of the prior art.

The preferred manner of forming the hooked end 40 and the needle rolling end 42 will now be described in connection with FIG. 12. The metal which is to be used to form the respective tips 14 and 12 is generally in the form of a solid conical rod which is cut a metal working saw or tool to form a cut or space 75. That is, the curved path of the cutting blades leaves a space 75 where there was previously metal and the cutting blade forms a larger diameter surface 46 on the hooked end and the smaller radius curved surface 47 on the upper tip 14 as shown in FIG. 12. The differences in the respective radii being determined by the width of the cutter blade. The curved surfaces 46 and 47 have a common center for their curvature but have different radii. The blank, i.e., the piece of metal, which is being cut to form the slot 75 is preferably rounded at the upper portion 79 adjacent where the slot 75 is to be formed and also rounded at the lower outer surface 80 to provide an outer curved 81 surface for the hooked end 40.

FIG. 13 is a diagramatic illustration showing that the needle actually rolling inwardly along the curved surface 46 by the needle rolling surface 47 until the needle becomes jammed between the surfaces 46 and 47, as above-described in connection with FIG. 5, whereupon the needle is tightly gripped with a wrench-like action which will hold the needle steady during its manipulation by the surgeon. The rotation may be only 90° or so if the surgeon lifts the central needle portion 15c from the table surface 34 and leaves the point 35 and thread end 36 on the table surface and then brings the upper tip 14 against the top surface of the central portion 15c and presses the tips toward one another whereby the pointed end 35 and threaded end 36 will swing upwardly from the table surface 34 to the position shown in FIG. 4. In other instances, the surgeon will lift the needle from the table surface 34 and allow the needle ends to rotate down to the position shown in FIGS. 3 and 5A before bringing the upper tip 14 against the curved needle central portion 15c to begin the 180° rotation to bring the needle to position shown in FIG. 5. Thus, the amount of rotation may vary.

From the foregoing, it will be seen that the present invention provides a new and improved needle holder microinstrument having fine pointed tips curved for automatically rotating microsurgical needles into an effective position without the use of a second forceps and the extra-manipulation by the second forceps. Also, it will be seen that the microsurgical instrument is a configured for a rotational technique of spinning the instrument as in the manner of a spindle between the thumb and the middle finger to cause the gripped needle to penetrate the tissue with a smooth precise motion. Additionally, the instrument is provided with alignment means which can readily align and continually align the microsurgical tips during the complete movement during the open and closed positions of the instrument; the alignment means does not interfere with the use of the rotational technique for the instrument.

While a preferred embodiment has been shown and described, it will be understood that there is no intent to limit the invention by such disclosure but, rather, it is intended to cover all modifications and alternate constructions falling within the spirit and scope of the invention as defined in the appended claims.

What is claimed is:

1. A hand-held surgical tool for turning and gripping microsurgical curved needles having ends, said tool comprising:
    an elongated body for grasping by the user and having a generally cylindrical central portion for spinning about a longitudinal axis through said body,
    spaced upper and lower tips on said body adapted to be moved toward each other to grip the needle,
    said tips terminating in sharp pointed ends, one of said ends on said first tip being a hooked end and having a first curved surface for hooking under a microsurgical needle and for holding the needle while it pivots its ends downwardly,
    said second end having a shorter length than said hooked end,
    said hooked end on said first tip extending beyond said second end and extending across the longitudinal axis and over said second end,
    a second curved surface on the end of the second tip facing the first curved surface to engage a side of the microsurgical needle when the tips are moved together,
    said second curved surface engaging and rolling the needle along the first curved surface to swing the ends upwardly as the tips are brought to the closed gripping position, said needle being held between said curved surfaces as the cylindrical central section is turned to spin the microsurgical needle ends in an arc.

2. The tool in accordance with claim 1 in which said first and second curved surfaces are curved in the fore and aft directions of the tips, said curved surfaces defining a straight transverse line for engaging the curved needle at outer edges of one tip with the curved needle being engageable at a curved center portion by the other tip.

3. The tool in accordance with claim 1 in which alignment means hold the tips in a given plane of movement between open and closed positions.

4. The tool in accordance with claim 3 in which the alignment means comprises a convolute spring having upper and lower coils connected to the first and second tips, respectively, said coils biasing the tips apart toward the open position.

5. The tool in accordance with claim 3 in which the alignment means comprises an elongated key and slot means on said tips for continuous and progressive engagement and disengagement in the open and closed positions as well as all intermediate positions as the tips open and close between the open and closed positions.

6. The tool in accordance with claim 1 including a rounded exterior end wall on the first tip opposite the first curved surface.

7. The tool in accordance with claim 1 in which said hooked end having a curved surface with a larger radiused curvature than the curved surface on said second tip.

8. A tool in accordance with claim 6 in which the respective curved surfaces on the first and second tips are spaced apart a distance substantially equal to the diameter of the needle so that the needle will be gripped therebetween.

9. A tool in accordance with claim 1 in which said curved surface on said hooked end has a radius in the range of 1 mm to 3 mm.

* * * * *